United States Patent
Fritzmeier et al.

(10) Patent No.: US 11,357,720 B2
(45) Date of Patent: Jun. 14, 2022

(54) SKIN CARE COMPOSITION

(71) Applicant: Georg Fritzmeier GmbH & Co. KG, Grosshelfendorf (DE)

(72) Inventors: Ursula Fritzmeier, Munich (DE); Birgit Lewandowski, Haar (DE)

(73) Assignee: GEORG FRITZMEIER GMBH & CO. KG, Grosshelfendorf (DE)

( * ) Notice: Subject to any disclaimer, the term of this patent is extended or adjusted under 35 U.S.C. 154(b) by 310 days.

(21) Appl. No.: 16/326,798

(22) PCT Filed: Aug. 16, 2017

(86) PCT No.: PCT/EP2017/070778
§ 371 (c)(1),
(2) Date: Feb. 20, 2019

(87) PCT Pub. No.: WO2018/036882
PCT Pub. Date: Mar. 1, 2018

(65) Prior Publication Data
US 2019/0183783 A1  Jun. 20, 2019

(30) Foreign Application Priority Data

Aug. 24, 2016 (DE) .................... 10 2016 115 680.9
Feb. 24, 2017 (DE) .................... 10 2017 103 850.7

(51) Int. Cl.
| | | |
|---|---|---|
| A61K 8/99 | (2017.01) | |
| A61K 8/73 | (2006.01) | |
| A61Q 19/00 | (2006.01) | |
| A61K 9/00 | (2006.01) | |
| A61K 47/36 | (2006.01) | |
| A61K 8/04 | (2006.01) | |
| A61K 8/06 | (2006.01) | |
| A61K 9/06 | (2006.01) | |
| A61K 9/107 | (2006.01) | |
| A61K 31/722 | (2006.01) | |
| A61K 31/728 | (2006.01) | |
| A61K 35/744 | (2015.01) | |
| A61K 35/747 | (2015.01) | |

(52) U.S. Cl.
CPC .............. *A61K 8/99* (2013.01); *A61K 8/042* (2013.01); *A61K 8/062* (2013.01); *A61K 8/735* (2013.01); *A61K 8/736* (2013.01); *A61K 9/0014* (2013.01); *A61K 9/0034* (2013.01); *A61K 9/06* (2013.01); *A61K 9/107* (2013.01); *A61K 31/722* (2013.01); *A61K 31/728* (2013.01); *A61K 35/744* (2013.01); *A61K 35/747* (2013.01); *A61K 47/36* (2013.01); *A61Q 19/005* (2013.01); *A61Q 19/007* (2013.01); *A61K 2800/75* (2013.01)

(58) Field of Classification Search
CPC .......... A61K 8/99; A61K 8/042; A61K 8/062; A61K 8/735; A61K 8/736; A61K 2800/75; A61K 31/722; A61K 31/728; A61K 35/744; A61K 35/747; A61K 47/36; A61K 9/0014; A61K 9/0034; A61K 9/06; A61K 9/107; A61Q 19/005; A61Q 19/007
See application file for complete search history.

(56) References Cited

FOREIGN PATENT DOCUMENTS

| | | | | |
|---|---|---|---|---|
| CA | 2948312 A1 | 11/2015 | | |
| EP | 2050434 A1 * | 4/2009 | .......... | A61K 35/747 |
| EP | 2050434 A1 | 4/2009 | | |
| EP | 2226068 A1 * | 9/2010 | .............. | A61K 8/99 |
| EP | 2226068 A1 | 9/2010 | | |
| EP | 1995307 B1 | 9/2014 | | |
| FR | 2889057 A1 | 2/2007 | | |

OTHER PUBLICATIONS

Al-Ghazzewi, F., Tester, R. Beneficial Microbes, vol. 5, No. 2, Jun. 1, 2014, pp. 99-107(9) (Year: 2014).*
Nadarajah, K. et al. Production of Chitosan by Fungi. Pakistan Journal of Biological Sciences (2001). 4 (3): 263-265 (Year: 2001).*
Tatu AL. The use of a topical compound cream product with chitosan, silver sulfadiazine bentonite hidrogel and lactic acid for the treatment of a patient with rosacea and ulcerated livedoid vasculopathy. Our Dermatol Online. 2015;6(4):456-459 (Year: 2015).*
Weindl, G. et al. Hyaluronic Acid in the Treatment and Prevention of Skin Diseases: Molecular Biological, Pharmaceutical and Clinical Aspects. Skin Pharmacol Physiol 2004;17:207-213. (Year: 2004).*
International Search Report and Written Opinion for PCT/EP2017/070778 dated Oct. 16, 2017 (13 pages; with English translation).
Database GNPD [Online] MINTEL; Jul. 2016 "Original Flavoured Yogurt", XP0027740002, Database accession No. 4181201 Ingredients (Standard form).
Georg Fuchs, Hans-Günter Schlegel, "Allgemeine Mikrobiologie", 8. Auflage, Thieme Verlag (2006), S. 354.
EPO Office Action for Application No. EP17754154.7 dated Nov. 4, 2019 (3 pages; English translation only).

* cited by examiner

*Primary Examiner* — Blaine Lankford
(74) *Attorney, Agent, or Firm* — Mindful IP PLLC

(57) ABSTRACT

A skin care composition includes a carrier substance and a proportion of lactic acid bacteria and/or their metabolic products, wherein the metabolic products are included in the skin care composition in a form of a ferment obtained during a cultivation of the lactic acid bacteria. The skin care composition additionally contains chitosan or a suitable chitosan derivative.

12 Claims, No Drawings

SKIN CARE COMPOSITION

CROSS-REFERENCE TO RELATED APPLICATIONS

This application is a national stage of, and claims priority to, Patent Cooperation Treaty Application No. PCT/EP2017/070778, filed on Aug. 16, 2017, which application claims priority to German Application No. DE 10 2016 115 680.9, filed on Aug. 24, 2016 and DE 10 2017 103 850.7, filed on Feb. 24, 2017, which applications are hereby incorporated herein by reference in their entireties.

DESCRIPTION

The disclosure relates to a skin care composition for treating dry skin and for relieving skin irritations.

Different care products are used for the care of dry skin or for relieving skin irritations such as erythema or itching, but they do not always show the desired care effect or relief.

In view of this, the disclosure is based on the object of creating a skin care composition with improved effect for dry skin care and for relieving skin irritations.

The presence of lactic acid bacteria in the normal flora of intestines, skin and mucous membranes in humans and animals as well as their involvement in the formation and maintenance of a so-called shield on the skin is known. The natural bacterial shield of the skin serves above all to prevent the growth of unwanted microorganisms and thus to prevent the risk of infection (Georg Fuchs, Hans-Gunter Schlegel, "Allgemeine Mikrobiologie" [General microbiology], 8th edition, Thieme Verlag (2006), p. 354).

Lactic acid bacteria as well as lactic acid are therefore used in medical products primarily to stabilize or restore the aforementioned shield function if it is impaired or lost. This is achieved by increasing and maintaining the lactic acid concentration on the treated skin or mucous membrane so that the physiological pH value is restored. Related products are, for example, vaginal capsules or vaginal suppositories containing lactic acid bacteria and/or lactic acid.

EP 1995307 B1 discloses methods and means of protecting the skin against pathogenic microorganisms. Specifically, microorganisms of the species *Lactobacillus buchneri* and *Lactobacillus delbrückii* are used in order to inhibit the growth of special pathogenic microorganisms without inhibiting the growth of *Staphylococcus epidermidis*, which are attributed to the resident skin flora.

Moreover, the use of lactic acid bacteria in toothpaste is known. The active ingredient Pro-t-Action® developed by BASF and obtained from lactic acid bacteria is added to prevent the caries-producing bacterium *Streptococcus mutans* from adhering to the teeth.

The use of lactic acid bacteria in products that are to be applied to the skin is limited according to the prior art to achieving or improving protection against pathogenic microorganisms. The relieving of skin irritations or a care effect for dry skin are not known from this.

The aforementioned object of the present disclosure is solved by a skin care composition with a carrier substance and a proportion of lactic acid bacteria and/or their metabolic products.

Surprisingly, it turned out that a skin care composition with lactic acid bacteria solves the problem mentioned at the beginning particularly well. The skin care composition according to the disclosure has an excellent effect for relieving skin irritations and is also excellently suited for the care of dry skin.

The lactic acid bacteria used in the present disclosure are cultivated in a generally known manner in a suitable nutrient solution. The *Lactobacillus* ferment thus obtained is then used in the preparation of the skin care composition according to the disclosure.

The skin care composition can contain the lactic acid bacteria alive or can contain only their metabolic products. In particular, the ferment obtained during the cultivation of the lactic acid bacteria is either used as such and thus together with the living cultures in the preparation of the skin care composition or the ferment obtained is subjected to a treatment before use which inactivates the living cultures, i.e. kills them. Examples include thermal sterilization processes, such as heat sterilization, and physical sterilization processes, such as radiation sterilization and sterile filtration.

In an example, the skin care composition according to the disclosure can contain both living cultures and inactive cultures of the lactic acid bacteria.

Preferably, the lactic acid bacteria are selected from one or more strains of *Lactobacillus casei, Lactobacillus apis, Lactobacillus gasseri, Lactobacillus sakei, Lactobacillus lactis, Lactobacillus gastricus, Lactobacillus fructosus, Lactobacillus plantarum, Lactococcus plantarum, Fructobacillus fructosus, Lactobacillus parabuchneri, Lactobacillus frumenti, Lactobacillus fermentum, Lactobacillus jensenii, Lactobacillus reuteri, Lactobacillus rhamnosus, Lactobacillus piscicola,* and *Lactobacillus murinus*.

Further preferred are the lactic acid bacteria selected from one or more strains of *Lactobacillus casei, Lactobacillus apis, Lactobacillus gasseri, Lactobacillus sakei, Lactobacillus lactis, Lactobacillus gastricus, Lactobacillus fructosus, Lactobacillus plantarum, Lactococcus plantarum, Fructobacillus fructosus, Lactobacillus parabuchneri, Lactobacillus frumenti, Lactobacillus fermentum, Lactobacillus jensenii,* and *Lactobacillus reuteri*.

Especially preferred are the lactic acid bacteria selected from one or more strains of *Lactobacillus casei, Lactobacillus apis, Lactobacillus gasseri, Lactobacillus sakei, Lactobacillus lactis, Lactobacillus gastricus, Lactobacillus fructosus, Lactobacillus plantarum, Lactococcus plantarum, Fructobacillus fructosus,* and *Lactobacillus* parabuchneri.

It is thereby most preferred when the lactic acid bacteria are from the strain *Lactobacillus plantarum*.

In order to ensure a sufficient effect of the skin care composition according to the disclosure, the mass fraction of lactic acid bacteria in the skin care composition according to the disclosure is at least 0.1%, preferably about 1% to 10% and especially preferred about 5%.

In another example, the skin care composition also contains chitosan or a suitable chitosan derivative such as chitosan lactate. Chitosan can also act as the carrier substance.

The skin care effect can be further improved if it also contains a proportion of hyaluronic acid or a suitable hyaluronic acid derivative.

The carrier substance is preferably a cream.

This cream can be based on an oil-in-water emulsion or suspension. A gel matrix can also be used.

The skin care composition according to the disclosure can, as explained above, be prepared in the form of a cream or gel. Further exemplary preparation types are a serum or a bath additive. A serum according to the disclosure is usually characterized by being liquid, and having a light texture as well as a relatively high active ingredient ratio. A bath additive according to the disclosure is usually also liquid.

According to another example, the skin care composition according to the disclosure can also be used for the production of a protective dressing or wound dressing. In this case, the composition according to the disclosure is introduced as a nurturing additive into a suitable carrier or is applied to it. The carrier containing the skin care composition according to the disclosure can be applied to the skin area to be cared for or treated. The materials normally used for dressings or wound dressings can be used as carriers, such as for example fabrics or nonwovens made of natural or artificial fibers or plastic films. The carrier can consist of a single layer or several layers, whereby these preferably consist of different materials.

Further advantages and features of the present disclosure result from the following detailed description, whereby additional reference is made to the examples.

In addition to lactic acid bacteria or their metabolic products, the skin care composition according to the disclosure may contain one or more components which support the effect of the skin care composition according to the disclosure or show a caring or soothing effect themselves. Among others, chitosan and hyaluronic acid can be mentioned here.

Furthermore, the skin care composition according to the disclosure may contain excipients commonly used in cosmetic articles such as solvents, humectants and moisturizers, emollients, emulsifiers, gelling agents, stabilizers, antioxidants and buffers. Water is the preferred solvent.

UV Erythema Test

The effectiveness of the skin care composition according to the disclosure was tested using a UV erythema test on human skin of six test subjects. For this purpose, the skin of each of the test persons was irradiated with UV-B light in such a way that a visible reddening (erythema) developed. The reddened skin areas were then treated daily with three different products A, B and C over a period of seven days, with a fourth skin area left untreated. The erythema was measured daily by a chromameter and subjectively evaluated by the test persons.

Product A was a cream containing living cultures of *Lactobacillus plantarum*, chitosan and water. Product B was a cream containing inactive (killed) cultures of *Lactobacillus plantarum*, chitosan and water. Products A and B contained the *lactobacillus* in a proportion of 0.3% (w/v) and chitosan in the form of chitosan lactate (molecular weight 30,000-500,000 Da) in a proportion of 10% (w/v). Product C was a commercially available cream containing dexpanthenol as an active ingredient (Bepanthen® from BASF) and was known as an effective reference product. The three products used in the test were packaged neutrally so that none of the persons involved in carrying out the tests could identify which of the products contained the ingredient to be tested or was a comparative sample.

In particular, four test fields each measuring 2 cm×2 cm were marked on the inside of the forearms of six probands of different skin types aged between 24 and 41 years. Irradiation with UV-B light was performed with the device UV802L/P/UV6 (Waldmann). For each proband, an individual irradiation time was chosen to generate visible erythema corresponding to 1.5 times their own MED (MED=minimum erythema dose—corresponds to the minimum dose until an erythema is reached). Each of the four test fields was irradiated with the same radiation intensity. Test fields A, B and C were treated with products A, B and C, respectively. Field D remained untreated for the duration of the test. The application of the preparations was started 24 hours after UV irradiation and then continued once a day.

The probands were instructed not to use any other care products or sunbathe during this time.

The colorimeter Chromameter CR 200 made by Minolta was used for the quantitative determination of the color changes in the human skin, here the erythema. For the measurement, a flexible measuring head (diameter 1 cm) is placed on the skin area to be tested and the color nuances of the skin are measured by emission of a light flash (CIE standard illuminant C). Three sensors measure the light reflected back from the skin and display it numerically in the L*a*b* color system. The color space of the L*a*b* system is characterized by the brightness L* (where 100=white; 0=black) and the color coordinates a* and b*, where the a* coordinate shows the red-green color and the b* coordinate shows the blue-yellow color. With increasing reddening of the skin, an increasing a* value indicates an increased red portion of the skin and a decreasing a* value indicates fading of the erythema. In order to minimize possible color fluctuations in the measuring field, three consecutive measurements were performed, which were averaged and stored by the device.

The measurements were performed once per day. In addition, each of the test persons gave a subjective evaluation regarding reddening, itching and effect of the respective test product. Table 1 shows the schedule of product applications, measurements and evaluations.

TABLE 1

2.1 Schedule of product applications, measurements and evaluations

| | Product applications | Diary (reddening, itching and effect) | Measurement |
|---|---|---|---|
| Day 0 (irradiation) | — | ✓ | ✓ |
| Day 1 (maximum erythema) | ✓ | ✓ | ✓ |
| Day 2 | ✓ | ✓ | ✓ |
| Day 3 | ✓ | ✓ | ✓ |
| Day 4 | ✓ | ✓ | ✓ |
| Day 5 | ✓ | ✓ | — |
| Day 6 | ✓ | ✓ | — |
| Day 7 | ✓ | ✓ | ✓ |

In dermatological examinations before, during, and after the test, none of the test subjects showed pathological skin changes in the region of the test area. The mentioned preparations were tolerated very well and did not lead to undesired skin changes in any of the test persons.

The following table 2 shows for the days 1, 2, 3, 4, and 7 the results of the erythema measured by the chromameter, whereby for each day an average value of the individual measurements of the six probands is given. Only the a* value is used, as this is the best reflection of the reddening of the skin.

For a better comparison of the strength of the erythema after irradiation, day 1 is given in relation to the a* value before irradiation. For days 2, 3, 4, and 7 the measured a* value is given in relation to the value of the maximum erythema (24 h after irradiation) to give a value corresponding to the relative decrease of the erythema.

TABLE 2

Summarized representation of chromameter measurements (a* value)

| | Comparison before irradiation/ 24 h after irradiation (max. erythema) | Comparison 24 h after irradiation (max. erythema)/ day 2 after irradiation (24 h after first product application) | Comparison 24 h after irradiation (max. erythema)/ day 3 after irradiation (48 h after first product application) | Comparison 24 h after irradiation (max. erythema)/ day 4 after irradiation (72 h after first product application) | Comparison 24 h after irradiation (max. erythema)/ day 7 after irradiation (144 h after first product application) |
|---|---|---|---|---|---|
| Product A | 57.65% | −8.24% | −12.76% | −17.69% | −22.55% |
| Product B | 67.46% | −10.80% | −17.10% | −22.31% | −23.51% |
| Product C | 62.57% | −11.63% | −18.04% | −24.66% | −29.13% |
| Field D (untreated) | 55.08% | −5.94% | −11.52% | −18.54% | −19.36% |

The following tables summarize the results of the subjective evaluations of the probands with regard to reddening, itching and the effect of the individual products. The evaluations are based on a 10-step scale (where 1=not present; 10=very strong; or for the effect of the product: 1=no noticeable effect; 10=very good effect).
In addition: *=before irradiation; **=maximum erythema.

TABLE 3.1

Subjective evaluation proband 1

| | Day 0* | Day 1** | Day 2 | Day 3 | Day 4 | Day 5 | Day 6 | Day 7 |
|---|---|---|---|---|---|---|---|---|
| Field A | | | | | | | | |
| Reddening | 1 | 6 | 5 | 4 | 3 | 2 | 2 | 1 |
| Itching | 1 | 2 | 1 | 1 | 1 | 1 | 1 | 1 |
| Effect of product | — | 1 | 3 | 2 | 2 | 2 | 1 | 1 |
| Field B | | | | | | | | |
| Reddening | 1 | 5 | 3 | 2 | 2 | 2 | 1 | 1 |
| Itching | 1 | 2 | 1 | 1 | 1 | 1 | 1 | 1 |
| Effect of product | — | 1 | 4 | 4 | 4 | 2 | 1 | 1 |
| Field C | | | | | | | | |
| Reddening | 1 | 5 | 4 | 3 | 2 | 2 | 1 | 1 |
| Itching | 1 | 2 | 1 | 1 | 1 | 1 | 1 | 1 |
| Effect of product | — | 1 | 3 | 3 | 4 | 2 | 1 | 1 |
| Field D | | | | | | | | |
| Reddening | 1 | 4 | 3 | 3 | 2 | 2 | 2 | 1 |
| Itching | 1 | 2 | 1 | 1 | 1 | 1 | 1 | 1 |

TABLE 3.2

Subjective evaluation proband 2

| | Day 0* | Day 1** | Day 2 | Day 3 | Day 4 | Day 5 | Day 6 | Day 7 |
|---|---|---|---|---|---|---|---|---|
| Field A | | | | | | | | |
| Reddening | 1 | 9 | 6 | 5 | 4 | 3 | 2 | 2 |
| Itching | 1 | 4 | 2 | 1 | 1 | 1 | 1 | 1 |
| Effect of product | — | 5 | 5 | 5 | 5 | 5 | 3 | 3 |
| Field B | | | | | | | | |
| Reddening | 1 | 9 | 7 | 6 | 4 | 4 | 2 | 2 |
| Itching | 1 | 4 | 2 | 1 | 1 | 1 | 1 | 1 |
| Effect of product | — | 5 | 4 | 4 | 4 | 4 | 3 | 3 |

TABLE 3.2-continued

Subjective evaluation proband 2

|  | Day 0* | Day 1** | Day 2 | Day 3 | Day 4 | Day 5 | Day 6 | Day 7 |
| --- | --- | --- | --- | --- | --- | --- | --- | --- |
| Field C |  |  |  |  |  |  |  |  |
| Reddening | 1 | 9 | 7 | 5 | 4 | 3 | 2 | 2 |
| Itching | 1 | 4 | 2 | 1 | 1 | 1 | 1 | 1 |
| Effect of product | — | 5 | 6 | 6 | 5 | 5 | 3 | 3 |
| Field D |  |  |  |  |  |  |  |  |
| Reddening | 1 | 9 | 8 | 6 | 5 | 4 | 3 | 2 |
| Itching | 1 | 4 | 2 | 1 | 1 | 1 | 1 | 1 |

TABLE 3.3

Subjective evaluation proband 3

|  | Day 0* | Day 1** | Day 2 | Day 3 | Day 4 | Day 5 | Day 6 | Day 7 |
| --- | --- | --- | --- | --- | --- | --- | --- | --- |
| Field A |  |  |  |  |  |  |  |  |
| Reddening | 1 | 4 | 4 | 3 | 2 | 2 | 1 | 1 |
| Itching | 1 | 4 | 2 | 1 | 1 | 1 | 1 | 1 |
| Effect of product | — | 1 | 2 | 3 | 4 | 2 | 1 | 1 |
| Field B |  |  |  |  |  |  |  |  |
| Reddening | 1 | 4 | 4 | 3 | 2 | 2 | 1 | 1 |
| Itching | 1 | 4 | 2 | 1 | 1 | 1 | 1 | 1 |
| Effect of product | — | 1 | 2 | 3 | 4 | 2 | 1 | 1 |
| Field C |  |  |  |  |  |  |  |  |
| Reddening | 1 | 4 | 4 | 4 | 3 | 2 | 2 | 2 |
| Itching | 1 | 4 | 1 | 1 | 1 | 1 | 1 | 1 |
| Effect of product | — | 1 | 3 | 3 | 5 | 3 | 4 | 3 |
| Field D |  |  |  |  |  |  |  |  |
| Reddening | 1 | 6 | 8 | 7 | 6 | 4 | 2 | 2 |
| Itching | 1 | 4 | 5 | 2 | 2 | 1 | 1 | 1 |

TABLE 3.4

Subjective evaluation proband 4

|  | Day 0* | Day 1** | Day 2 | Day 3 | Day 4 | Day 5 | Day 6 | Day 7 |
| --- | --- | --- | --- | --- | --- | --- | --- | --- |
| Field A |  |  |  |  |  |  |  |  |
| Reddening | 1 | 9 | 5 | 4 | 3 | 2 | 2 | 2 |
| Itching | 1 | 5 | 2 | 1 | 1 | 1 | 1 | 1 |
| Effect of product | — | 2 | 4 | 7 | 7 | 7 | 7 | 7 |
| Field B |  |  |  |  |  |  |  |  |
| Reddening | 1 | 9 | 6 | 5 | 3 | 2 | 2 | 1 |
| Itching | 1 | 5 | 2 | 1 | 1 | 1 | 1 | 1 |
| Effect of product | — | 2 | 3 | 5 | 7 | 7 | 7 | 8 |
| Field C |  |  |  |  |  |  |  |  |
| Reddening | 1 | 9 | 7 | 7 | 5 | 4 | 3 | 2 |
| Itching | 1 | 5 | 2 | 1 | 1 | 1 | 1 | 1 |
| Effect of | — | 2 | 2 | 4 | 5 | 5 | 6 | 7 |

TABLE 3.4-continued

| | \multicolumn{7}{c}{Subjective evaluation proband 4} |
|---|---|---|---|---|---|---|---|
| | Day 0* | Day 1** | Day 2 | Day 3 | Day 4 | Day 5 | Day 6 | Day 7 |
| product |
| Field D |
| Reddening | 1 | 9 | 7 | 7 | 5 | 4 | 3 | 2 |
| Itching | 1 | 5 | 2 | 1 | 1 | 1 | 1 | 1 |

TABLE 3.5

| | \multicolumn{7}{c}{Subjective evaluation proband 5} |
|---|---|---|---|---|---|---|---|
| | Day 0* | Day 1** | Day 2 | Day 3 | Day 4 | Day 5 | Day 6 | Day 7 |
| Field A |
| Reddening | 1 | 7 | 4 | 3 | 3 | 2 | 2 | 1 |
| Itching | 1 | 4 | 2 | 1 | 1 | 1 | 1 | 1 |
| Effect of product | — | 2 | 5 | 5 | 4 | 2 | 2 | 2 |
| Field B |
| Reddening | 1 | 8 | 6 | 5 | 4 | 2 | 2 | 1 |
| Itching | 1 | 4 | 2 | 1 | 1 | 1 | 1 | 1 |
| Effect of product | — | 2 | 4 | 4 | 4 | 2 | 2 | 2 |
| Field C |
| Reddening | 1 | 6 | 4 | 3 | 2 | 2 | 2 | 1 |
| Itching | 1 | 3 | 2 | 2 | 1 | 1 | 1 | 1 |
| Effect of product | — | 2 | 5 | 5 | 4 | 2 | 2 | 2 |
| Field D |
| Reddening | 1 | 5 | 4 | 4 | 4 | 3 | 2 | 2 |
| Itching | 1 | 3 | 3 | 2 | 2 | 1 | 1 | 1 |

TABLE 3.6

| | \multicolumn{7}{c}{Subjective evaluation proband 6} |
|---|---|---|---|---|---|---|---|
| | Day 0* | Day 1** | Day 2 | Day 3 | Day 4 | Day 5 | Day 6 | Day 7 |
| Field A |
| Reddening | 1 | 5 | 4 | 2 | 2 | 2 | 1 | 1 |
| Itching | 1 | 3 | 2 | 1 | 1 | 1 | 1 | 1 |
| Effect of product | — | 1 | 1 | 5 | 5 | 3 | 1 | 1 |
| Field B |
| Reddening | 1 | 5 | 4 | 2 | 2 | 2 | 1 | 1 |
| Itching | 1 | 3 | 2 | 1 | 1 | 1 | 1 | 1 |
| Effect of product | — | 1 | 1 | 5 | 5 | 3 | 1 | 1 |
| Field C |
| Reddening | 1 | 8 | 8 | 5 | 4 | 3 | 2 | 1 |
| Itching | 1 | 4 | 2 | 1 | 1 | 1 | 1 | 1 |
| Effect of product | — | 1 | 1 | 5 | 5 | 4 | 2 | 1 |
| Field D |
| Reddening | 1 | 8 | 8 | 5 | 4 | 4 | 1 | 1 |
| Itching | 1 | 4 | 3 | 1 | 1 | 1 | 1 | 1 |

The results of the chrometer measurements (a* value) presented in table 1 clearly show that, in comparison to the untreated test field, a reddening-reducing effect was observed for all products.

The subjective evaluations of the six probands also show that the reddening decreased faster due to the application of the products and that in some cases (probands 3 and 5) the itching lasted for a shorter time. In addition, the effect of the products A and B according to the disclosure, which contained living or inactive cultures of *Lactobacillus plantarum*, was generally assessed by the probands as having at least the same positive effect as the commercial product C with the active ingredient dexpanthenol, which is known to work well. A further advantage of the skin care composition according to the disclosure is that the addition of a synthetic active ingredient is not necessary.

It could thus be shown that a skin care composition according to the present disclosure has an effect of relieving skin irritations. Such a composition also has the advantage that it can be easily produced and is also suitable for the care of dry skin.

Disclosed is a skin care composition with a carrier substance and a proportion of lactic acid bacteria or their metabolic products.

The invention claimed is:

1. A skin care composition comprising a carrier substance and a proportion of lactic acid bacteria and their metabolic products, wherein:
    the metabolic products are included in the skin care composition in a form of a ferment obtained during a cultivation of the lactic acid bacteria;
    the lactic acid bacteria are selected from one or more strains included in a set of *Lactobacillus casei, Lactobacillus apis, Lactobacillus gassed, Lactobacillus sakei, Lactobacillus lactis, Lactobacillus gastricus, Lactobacillus fructosus, Lactobacillus plantarum, Lactococcus plantarum, Fructobacillus fructosus*, and *Lactobacillus parabuchneri*;
    a mass fraction of the lactic acid bacteria is in a range from 5% to 10%;
    the skin care composition additionally contains chitosan or a suitable chitosan derivative; and
    the carrier substance is a cream.

2. The skin care composition according to claim 1, wherein the lactic acid bacteria are contained in a form of living cultures.

3. The skin care composition according to claim 1, wherein the lactic acid bacteria are contained in a form of inactive cultures.

4. The skin care composition according to claim 1, containing a proportion of hyaluronic acid.

5. The skin care composition according to patent claim 1, wherein the cream is based on an oil-in-water emulsion or dispersion or a gel matrix.

6. The skin care composition according to claim 1, wherein the lactic acid bacteria are of the strain *Lactobacillus plantarum*.

7. The skin care composition according to claim 6, wherein the lactic acid bacteria are contained in a form of living cultures.

8. The skin care composition according to claim 6, wherein the lactic acid bacteria are contained in a form of inactive cultures.

9. The skin care composition according to claim 6, containing a proportion of hyaluronic acid.

10. The skin care composition according to patent claim 6, wherein the cream is based on an oil-in-water emulsion or dispersion or a gel matrix.

11. A skin care composition comprising a carrier substance, a proportion of lactic acid bacteria and a ferment obtained during a cultivation of lactic acid bacteria including metabolic products of lactic acid bacteria, wherein:
    the lactic acid bacteria are selected from one or more strains included in a set of *Lactobacillus casei, Lactobacillus apis, Lactobacillus gasseri, Lactobacillus sakei, Lactobacillus lactis, Lactobacillus gastricus, Lactobacillus fructosus, Lactobacillus plantarum, Lactococcus plantarum, Fructobacillus fructosus*, and *Lactobacillus parabuchneri*;
    a mass fraction of the lactic acid bacteria is in a range from 5% to 10%;
    the skin care composition additionally contains chitosan or a suitable chitosan derivative; and
    the carrier substance is a cream.

12. A skin care composition comprising a carrier substance, a proportion of lactic acid bacteria and a ferment obtained during a cultivation of lactic acid bacteria including metabolic products of lactic acid bacteria, wherein:
    the lactic acid bacteria are selected from one or more strains included in a set of *Lactobacillus casei, Lactobacillus apis, Lactobacillus gasseri, Lactobacillus sakei, Lactobacillus lactis, Lactobacillus gastricus, Lactobacillus fructosus, Lactobacillus plantarum, Lactococcus plantarum, Fructobacillus fructosus*, and *Lactobacillus parabuchneri*;
    the lactic acid bacteria are inactive;
    a mass fraction of the lactic acid bacteria is in a range from 5% to 10%;
    the skin care composition additionally contains chitosan or a suitable chitosan derivative; and
    the carrier substance is a cream.

* * * * *